United States Patent [19]

Jelliffe et al.

[11] 4,308,866

[45] Jan. 5, 1982

[54] INFUSION CONTROLLING APPARATUS AND METHOD

[75] Inventors: Roger W. Jelliffe, Pasadena; Jack D. Crone, Sunland, both of Calif.

[73] Assignee: University of Southern California, Los Angeles, Calif.

[21] Appl. No.: 957,258

[22] Filed: Nov. 2, 1978

[51] Int. Cl.$^3$ ............................................. A61M 5/00
[52] U.S. Cl. ................................. 128/214 E; 364/413
[58] Field of Search ............... 128/214 E, 748, 214 C, 128/214 F; 364/413, 510

[56] References Cited

U.S. PATENT DOCUMENTS

| | | | |
|---|---|---|---|
| 3,809,871 | 5/1974 | Howard et al. | 128/214 E |
| 3,946,731 | 3/1976 | Lichtenstein | 128/214 E |
| 4,080,966 | 3/1978 | McNally et al. | 128/214 F |
| 4,094,318 | 6/1978 | Burke et al. | 128/214 E |
| 4,114,188 | 9/1978 | Carter et al. | 128/748 |
| 4,151,845 | 4/1979 | Clemens | 128/214 E |
| 4,165,532 | 8/1979 | Kendall et al. | 364/510 |
| 4,184,815 | 1/1980 | Casson et al. | 128/214 F |

OTHER PUBLICATIONS

Fukui, Y. et al., "Digital and Sampled-Data Control of Arterial BP During Halothane Anesthesia", Proc. San Diego Biomed. Symp. 1974, pp. 273-278.
Auto-Syringe Inc., General Informational Brochure for Models AS*2B, AS*2C, AS*2F, AS*3B, AS*5B, Hooksoft.
"A Device for the Precise Reg. of Blood Press. in Patients During Surg. and Hypertensive Crises", R. T. McNally et al., San Diego Biomed. Symposium, Feb. 2-4, 77, vol. XVI (1977), pp. 419-424.
"Regulation of Mean Arterial Pressure by Comp. Control of Vasoactive Agents in Post-Op. Patients", *Computers in Cardiology*, 1975, pp. 91-94.
"Therap. Uses of Na Nitroprusside and an Automated Method of Administration", A. D. Ivankovich, Ed. International Anesthesiology Clinics, Little Brown, vol. 16, #2, 1978, pp. 51-88.
Operating Instructions and Specs. for IMED, Mod. 929, Computer Controlled Infusion Pump, 6/1979.
Calfee, R. V. et al., "Closed Loop Control of Blood Pressure in Hypertensive Crisis", 30th ACEMB Los Angeles, Cal., Nov. 5-9, 1977, p. 388.
"An Optimal Expotential Intravenous Infusor", Collins et al., 30th ACEMB, Nov. 5-9, 1977, section 13.2.
"Dose-Regulated Penthane (Methoxyflurane) Anesthesia", Harry Lowe, 1977, pp. 99-109, Chapt. 7, Auto. Programmed Anesthesia.
*Products for Science*—Cole-Parmer Inst. Co., Masterflex ® pumps, p. 11.
"A Package of Time Shared Computer Programs for Patient Care", Jelliffe et al., pp. 154-162, Published in or after 1976.
"Clinical Studies with Computer-Assisted Lidocaine (L) Infusion Regimens", Circulation, vol. 54, No. 4, Sup. II, p. 211, 1976, Jelliffe et al.
"An Improved Computer Program for Lidocaine Infusion Regimens", Clinical Research, vol. 23, p. 125A, Feb. 1975, Jelliffe et al.
"A Computer Program for Xylocaine Infusion Regimens", Federation Proceedings, vol. 32, No. 3, p. 812, Aab, 1973, Jelliffe.
Research Inc. Catalog-Data-Trak ® Model 5500.

*Primary Examiner*—Lee S. Cohen
*Assistant Examiner*—Francis J. Jaworski
*Attorney, Agent, or Firm*—Nilsson, Robbins, Dalgarn, Berliner, Carson & Wurst

[57] ABSTRACT

Portable electronic medical apparatus for controlling the flow rate of a fluid for medically treating a patient may receive flow rate information representing sequences of up to 20 flow rates and their durations from an individual and from an electronic data processor, and operate continuously without the presence of an operator for in the range of 40 hours. Upon the incorporation of an infusion pump into the apparatus, the desired regimen of treatment may be accomplished; and through a keyboard input for the apparatus, an operator may in certain respects modify a regimen which is being carried out. Safety features in the apparatus include: a frequency detector for monitoring the frequency of a clocking signal for the apparatus; the selective testing of output signals of the apparatus, the portable power supply for the apparatus and the frequency detector against stored predetermined standards; and the provision of warning signals to an operator to indicate divergences from such standards. Additionally, fail safe signals for the apparatus are coupled to relay circuitry to interrupt the output of the apparatus if a central processing unit for the apparatus enters undesired modes of operation.

24 Claims, 3 Drawing Figures

INFUSION CONTROLLING APPARATUS AND METHOD

FIELD OF THE INVENTION

The invention pertains to apparatus employed in medically treating a patient, more particularly such apparatus which is employed to regulate the flow rate of a fluid used in treating a patient.

BACKGROUND OF THE INVENTION

The progress of medicine over the years may perhaps somewhat inaccurately but usefully be thought of in terms of its progress from an "art" toward a "science". The development annd systematizing of information used in treating patients with drugs intravenously and through inhalation is particularly interesting. Computer programs which provide regimens of drug treatment based on systematized information and characteristics of a particular patient have in fact provided doctors in a number of instances with the capability to approach more closely the goals of such treatment while avoiding the pitfalls and dangers (e.g. inadequate or toxic levels of the drug in the bloodstream). See, e.g. R. W. Jelliffe, J. Rodman, and E. Kolb, "Clinical Studies with Computer-Assisted Lidocaine (L) Infusion Regimens", *Circulation*, Vol. 54, No. 4, Suppl. II, p. 211, 1976; R. W. Jelliffe, F. Goicoechea, D. Tuey, M. Wyman, J. Rodman and B. Goldreyer, "An Improved Computer Program for Lidocaine Infusion Regimens", *Clinical Research*, Vol. 23, p. 125A, February 1975; and R. W. Jelliffe, "A Computer Program for Xylocaine Infusion Regimens", *Federation Proceedings*, Vol. 32, No. 3, p. 812 Aab, 1973.

Focusing, by way of example, on the drug lidocaine and its use in the treatment of heart attack victims, an historical problem has been achieving sufficient serum levels as early as possible during the first hours of treatment and then reaching and maintaining a target serum level. At the same time, one of course wishes to avoid serum levels which are toxic or which approach toxicity. These goals are of course contradictory in nature, particularly in light of the problem of obtaining a uniform distribution of the drug in the bloodstream and the related delayed reaction of a patient to a change in the infusion rate. As indicated by the above references, computer programs are of significant value in balancing such goals. Further, in response to the requirements which may be called for by such programs, and also as a general matter, a capability to regulate a rate of flow of a drug to a patient in a somewhat automatic, systematic and safe fashion is of great interest to medical practitioners. This is particularly true if a capability to incorporate a large number of frequent changes, or to "fine tune", is included.

The opportunity to free medical personnel for other tasks to the extent that such drug treatment regimens can be mechanized has been somewhat recognized. For example, apparatus has been developed which employs a chart coated with a conductive material and a probe which will follow a curve scratched along the surface of the chart when the chart is placed on a rotating drum to move the curve past the probe. This apparatus may then be used in conjunction with e.g. an anesthesia pump. See catalog and specification material related to Qan, Inc. Dose Regulated Anesthesia Pump (Mark II) and Research, Inc. Model 5500 Data Trak Programmer incorporated in such pump; and H. J. Lowe, Ch. 7—'Automated Programmed Anesthesia", in *Dose-Regulated Penthane (Methoxyflurane) Anesthesia*, Abbott Laboratories, 1972. The scratched curve creates two isolated planes along the chart which become electrically energized with oppositely phased AC voltages when the chart is placed on the drum. The probe then seeks the zero potential scratched curve, and as it moves along the curve is used to mechanically adjust a potentiometer and thus affect an electrical signal.

A related but quite different approach employs the incorporation of the control of in-house, e.g. in hospitals, devices to control fluid flow rates, such devices themselves under the control of in-house computers. Such in-house systems are particularly adapted to a so-called closed loop operation involving evaluation by the computer of the condition of the patient being treated during such treatment, and adjustment under the control of the computer in light of such condition. Exemplary of this approach is a computer controlled intensive care unit at the University of Alabama Medical Center.

SUMMARY OF THE INVENTION

The present invention is directed to an apparatus and method for controlling the flow rate of a fluid for medically treating a patient, incorporating types and degrees of flexibility and safety of great interest and value to medical practitioners.

Such apparatus has the flexibility to control the flow rate of a fluid according to fluid flow rate information available from an individual, and available from a source electronic data processor, the available information representing sequences of flow rates and their durations. Thus, in accordance with the invention, such apparatus includes: operator input means for receiving flow rate information provided by the individual and for providing electrical signals representative of the information; source processor input means for receiving flow rate information provided by the source processor and for providing electrical signals representative of the information; and electronic data processing means for receiving such electrical signals, for providing and storing storage signals representative of such signals and for providing flow rate output signals, representative of the storage signals, for regulating the flow rate of the fluid. Regulator means may then be incorporated into the apparatus for regulating the flow rate of the fluid in response to the output signals. Similarly, the source processor input means may include means for electrically coupling the apparatus to and decoupling the apparatus from the source electronic data processor; and the electronic data processing means may include a portable power supply having a power capacity sufficient to power the apparatus.

Along related lines, and in accordance with the invention, a method of regulating the flow rate of a fluid for medically treating a patient may then include the steps of: coupling portable electronic control apparatus to an electronic information source having information representative of a sequence of fluid flow rates and their durations; providing the control apparatus with the sequence information; decoupling the control apparatus and source; transporting the control apparatus to the vicinity of a patient requiring medical treatment with the fluid; coupling the apparatus to a supply of the fluid; and regulating the flow rate of the fluid according to the sequence information. The method may then include the additional step of modifying the regulating to differ from the sequence while regulating according to the sequence, for example under the control of an operator of the apparatus.

Returning to the apparatus, in accordance with other, including certain flexibility, features of the invention, medical apparatus for controlling the flow rate of a fluid for medically treating a patient includes: storage means for storing electrical signals representative of a sequence of at least 8 discrete flow rates for the fluid and their durations; and execution means for automatically providing output signals corresponding to the sequence in response to the stored signals, upon initiation of such providing by the execution means; and a portable power supply having a power capacity sufficient to power the apparatus. It is noted that the discreteness of the flow rates is indicative of digital apparatus and the advantages thereof, while the number of fluid flow rates is indicative of a capability to approach the advantages of continuous variation, simple or complex, in a digital environment. It is additionally noted that the human mind is not psychologically adapted to readily remember more than 6 or 7 times. This is evidenced, for example, by telephone numbers. Also, a number of flow rates greater than 6, 7 or 8, e.g. 12 or 20, may of course be required for complex cases. Related to such features, and in accordance with method aspects of the invention, a method of regulating the flow rate of a fluid for medically treating a patient includes the step of providing an electrical signal representative of a sequence of at least 8 discrete fluid flow rates and their durations. The signal may then, for example, be independent of the condition of the patient; and the duration of the sequence may, for example, be for at least 8 hours.

In accordance with yet other apparatus aspects, including safety features, of the invention, medical apparatus for controlling the flow rate of a fluid for medically treating a patient includes: storage means for storing electrical signals representative of a sequence of discrete flow rates for the fluid and their durations; and execution means for providing output signals corresponding to the sequence in response to the storage signals; wherein the execution means includes means for providing a clocking signal for the execution means, and a frequency detector for providing an output signal representative of the frequency of the clocking signal. The execution means may then further include means for selectively testing the output signals of the execution means and frequency detector against predetermined standards and for providing a warning signal in the event of a divergence from such standards. In accordance with yet other apparatus aspects, including other safety features, such medical apparatus includes: storage means, as above; and execution means for providing output signals in response to the storage signals, as above, and for further providing at least one control signal for indicating an undesired mode of operation for the execution means; wherein the execution means includes means for interrupting the provision of the output signals in response to an indication of an undesired mode of operation by the control signal.

In an embodiment, output signals for transmittal to an infusion pump, of a power supply, and of a frequency detector monitoring a clocking signal frequency, may be selectively tested against predetermined standards, and provision is made for warning signals to an operator, controlled by the outcome of such testing.

BRIEF DESCRIPTION OF THE DRAWINGS

In the drawings, exemplary embodiments demonstrating the various objectives and features hereof are set forth as follows.

DESCRIPTION OF ILLUSTRATIVE EMBODIMENTS

As indicated above, detailed illustrative apparatus and method embodiments of the invention are disclosed herein. However, embodiments may be constructed and performed in accordance with various forms and acts, some of which may be rather different from the disclosed illustrative embodiments. Consequently, the specific structural, functional and performance details disclosed herein are merely representative, yet in that regard are deemed to provide the best embodiments for purposes of disclosure and to provide a basis for the claims herein which define the scope of the present invention.

Figure 1A:
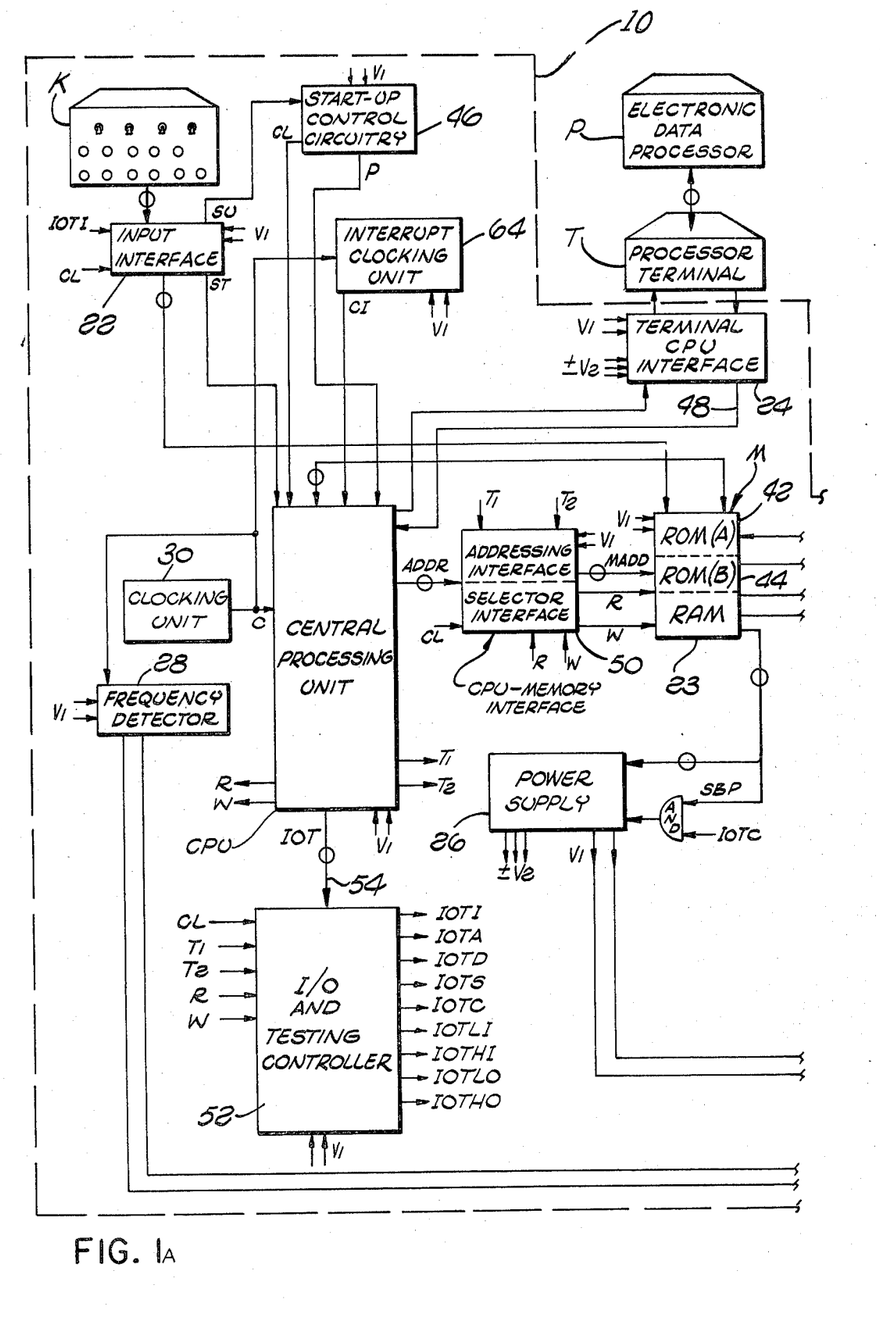
FIGS. 1A and 1B are a block diagram showing medical apparatus in accordance with the invention in the context of a system incorporating the regulated provision of a fluid for medically treating a patient.
Figure 1B:
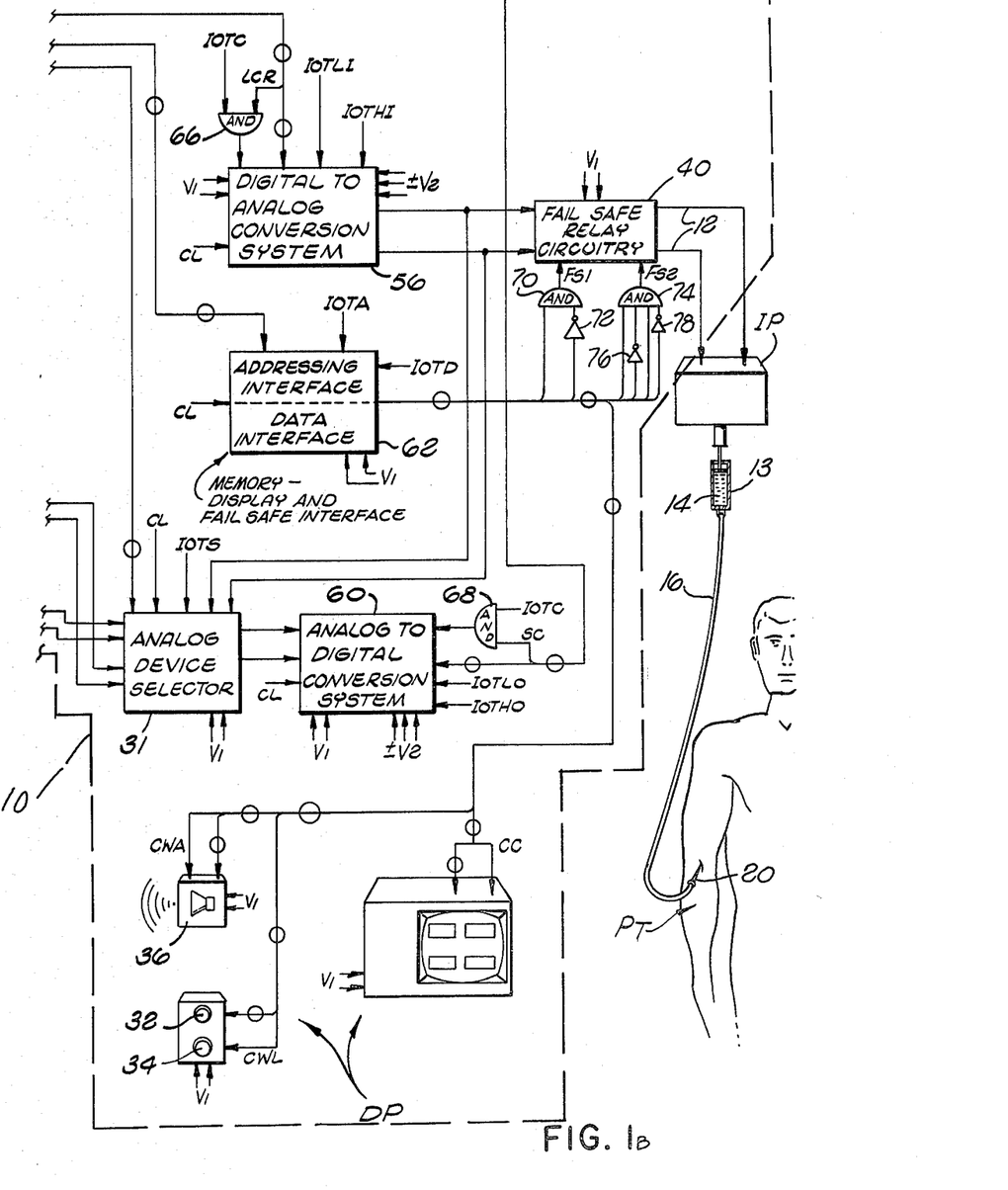

In FIG. 1, apparatus 10, in the context of a system, is shown which is particularly adapted to receive information representative of sequences of fluid flow rates, such information being provided by an individual through a keyboard K, incorporated into the apparatus, and/or by an electronic data processor P through a terminal T for the processor; to store digital signals representative of such sequence information in a memory M; and to provide generally analog output signals, representative of such sequence information which may be stored, for driving an infusion pump IP through output lines 12. The infusion pump IP in turn mechanically controls the flow rate of a fluid from a syringe-type, storage-drive 13 for a supply of fluid 14 which is intravenously infused into the bloodstream of a patient PT through a tube 16 and a needle 20 penetrating the bloodstream of the patient. A Harvard Model 2620 infusion pump, for example, is particularly well adapted to implementing the function of the infusion pump IP of FIG. 1.

An input interface 22 receives the flow rate information provided by the individual through the keyboard K and provides digital electrical signals representative of the information to the memory M. The flow rate information so provided is received and stored in a random-access portion 23 of the memory M (RAM). Along somewhat similar lines, flow rate information provided by the electronic data processor, which in turn is provided by the processor terminal T, is received for input into the apparatus 10 by a terminal-CPU interface 24 which provides digital electrical signals representative of such information to a central processing unit CPU, which places the flow rate information (and other types where necessary) in a form compatible for the memory M and for operational use by the apparatus 10 before providing the flow rate information (in digital form) to the RAM 23 for storage.

While the apparatus 10 is operating to provide its output to the infusion pump IP, various safety functions are carried out by the apparatus. Such functions include the selective testing of the output of the apparatus, of a power signal V1 for the apparatus from a portable power supply 26, and of the output signal of a frequency detector 28, representative of the frequency of a clocking unit 30 for the apparatus. The selective testing is carried out by the selection of the signal to be tested by an analog device selector 31 according to signal-represented information from the memory M, and the conversion of the generally analog signal to a digital representation for comparison with digitally-represented standards for such signals stored in the memory. Warning signals, implemented alphanumerically in a display panel DP, through display panel warning lights 32 and 34 and through a display panel sound alarm 36 (for warnings related to these and other functions), are employed to warn an operator of divergences from such standards. (As is indicated in FIG. 1, the warning lights, sound alarm and a visual display, all addressed in detail subsequently, are in a common display panel.) In addition, the absence of a high pulse along either of the control signals FS1 and FS2, over an unexpectedly long interval, such absence being in certain circumstances indicative of an undesired mode of operation for the central processing unit CPU, will cause a relay associated with the signal in fail safe relay circuitry 40 to open and interrupt the provision of the output of the apparatus to the infusion pump IP.

Typically, either the electronic data processor P or the keyboard K is used to provide a sequence of up to 20 flow rates and their durations. In this regard, a conventional program is incorporated in a first read-only portion 42 of the memory M (ROM(A)) to interact with the electronic data processor P through the central processing unit CPU, terminal-CPU interface 24 and processor terminal T. A conventional, monitor program, e.g. implemented on a 512 word read-only memory portion, having 8-bit words, may be conveniently used in the apparatus, for implementing the interaction. Also, the communication between the electronic data processor P and the processor terminal T might be conveniently implemented over a telephone line, the terminal then having an acoustic to digital transducer to permit intercommunication between the electronic data processor P and the apparatus. The terminal-CPU interface 24 then may be readily implemented using the well known RS-232C communication protocol in the interface 24. With a view toward flexibility and toward compatibility with the above, in the system of FIG. 1 it may then be assumed that the information received by the interface 24 and provided to the central processing unit CPU of the interface is in the American Standard Code for Information Interchange (ASCII), and that such information is converted by the central processing unit to a form for storage in the RAM 23. In the system of FIG. 1, this form is, along conventional lines, assumed to be standard binary coded decimal (in some cases, e.g. a signal-represented flow rate about to be used, converted to standard binary by the central processing unit and also stored in that form for immediate use), and a RAM 23 having a capacity of 256 8-bit words is deemed adequate for the 20 flow rates and durations and for other signals which the RAM 23 is employed to store.

A second read-only portion 44 of the memory M (ROM(B)) is employed to store another conventionally-implemented program for controlling the interaction of the apparatus with, ultimately, the individual who might provide sequence information, and for controlling the operation of the apparatus in accordance with sequence information and, generally, in accordance with the various safety and related functions of the apparatus. A capacity of 4096 8-bit words is certainly adequate for the ROM(B) 44, and a capacity of half that size is considered at least marginally sufficient.

During the provision of initial sequence information through the keyboard K, a digitally-represented data signal (e.g., a number in a flow rate sequence) or a digitally-represented input control signal may be stored in an input register in the input interface 22. The transmission of such a stored, digitally-represented signal, however, is controlled by the occurrence of a pulse along an apparatus control signal IOTI, as indicated in FIG. 1, which will not occur unless a status signal ST from the interface (caused to go high by receipt of an input by the interface) to the central processing unit CPU indicates that a new input has occurred. The presence of a subsequent digitally-represented input control signal (e.g., ENTER) in the input register in the interface 22, indicating that the individual has decided to enter the just-provided input for incorporation into the operation of the apparatus, will permit such incorporation. Alternatively, such incorporation might be blocked by, e.g., a CLEAR signal entered subsequently to the prior input signal, but before an ENTER signal has been provided to the input register.

The apparatus is programmed (ROM(B) 44) to provide the control signal IOTI (if the status signal ST is high) at intervals both during an initial input procedure from the keyboard K and during operation of the apparatus to regulate the flow rate of the fluid 14. This will be treated in somewhat more detail below. However, for present purposes it is emphasized that the occurrence of this signal during such operation enables the incorporation into such operation of modifications in an initially input flow rate sequence during the performance of the sequence by the apparatus. For safety, among other reasons, it is considered beneficial, however, to provide only a limited capability for such modifications. More specifically, through the program in the ROM(B) 44, the incorporation of a GO TO modification of a previously input sequence during the performance of the sequence or an ADJUST modification during such sequence are considered beneficial and consistent with safety requirements. The GO TO with the related data is to provide a jump to the beginning of a subsequent or earlier infusion number in the sequence and to continue the sequence from that point (or to the beginning of the current infusion number to continue, starting at the beginning of the running of the time for that number). The ADJUST is to adjust the current and all subsequent flow rates by a multiplication factor ranging, e.g., from 0.1 to 9.9.

The apparatus is adapted to implement such modifications, through keyboard input of data and input control signals (e.g., GO TO and ADJUST), which interact with, e.g. the ENTER and CLEAR input control signals, along the lines noted above, independently of whether the initial sequence information was provided through the keyboard K or by the processor P. The changes are of course implemented through the eventual storage of digitally-represented modification signals in the RAM portion of the memory M, e.g., during the regulation of the flow rate of the fluid 14.

Before proceeding to the operation of the apparatus of FIG. 1 as it regulates the flow rate of the fluid 14, it might be noted that in FIG. 1, the communication between the processor terminal T and the terminal-CPU interface 24 is serial, i.e. one bit at a time (e.g., in the ASCII code). Similarly, the communication between the terminal-CPU interface 24 and the central processing unit CPU is also serial (e.g., also in ASCII). Thus, although many of the apparatus control signals (to be described, being somewhat analogous to the apparatus control signal IOTI) which occur during such regulating operation of the apparatus will also occur while the processor P and the apparatus are interacting during the receipt of initial sequence data by the apparatus, the actual operation inside the central processing unit CPU during such receipt will not be typical of the regulating operation mode. Thus, during such receipt of initial sequence information provided by the processor P, the central processing unit CPU will be interacting with the processor P, receiving digitally-represented information provided serially, and interpreting that information and translating at least some of the information into, e.g., standard binary coded decimal.

Also, before proceeding to the regulating operation of the apparatus, it will be appropriate to describe the mode of start-up of the apparatus and several other aspects of the apparatus.

In the apparatus of FIG. 1, start-up is accomplished through conventionally-implemented apparatus and interactions, including start-up control circuitry 46. Start-up is initiated by a pushing of, e.g. a POWER keyboard button, resulting in a high pulse along a start-up signal SU, which in turn causes a high pulse along a clearing signal CL from the start-up control circuitry 46 to the central processing unit CPU and a number of other elements of FIG. 1. This clearing signal CL is employed to clear stale signal-represented information in the central processing unit and various of the other elements which should be cleared prior to start-up. The clearing may for example be accomplished along the rising edge of the high pulse along the control signal CL. Other modes for these signals and for such start-up will be readily apparent. In FIG. 1, the start-up control circuitry 46 includes a capacitor-resistor interaction to delay, e.g. for 2 milliseconds, the rising of another start-up signal P to a level sufficient to transfer control to the central processing unit CPU. Following such transfer of control, as a safety precaution of particular concern in medical apparatus, the integrity of each RAM storage location may be checked under the control of start-up aspects incorporated into the ROM(A) program, prior to the receipt of processor or keyboard provided sequence information. By integrity, is meant the capability of such storage location to have signal-represented information written into it and read out of it. In the event of a problem in this regard, a warning signal may be provided generally along lines described in another context below, and, for example, the program may deactivate the apparatus (or provide a zero output). The central processing unit CPU will in the absence of an indication to the contrary (next paragraph) assume that it is to receive initial input flow rate information from an individual through the keyboard K. In this "keyboard" case, a "keyboard-case" word in the memory M will be addressed to start the receipt of such information.

In the processor input, or "processor", case, the central processing unit CPU will sense through a signal along a serial input line 48 from the terminal-CPU interface 24, controlled by the electronic data processor P, that the apparatus has been electrically coupled to the processor P to receive flow rate sequence information from the processor. In this case, the central processing unit CPU will start the receipt of information by addressing another "processor-case" word in the memory M. The electronic data processor P, central processing unit CPU and ROM(A) program can then interact to provide the RAM with the sequence information from the electronic data processor P. The sequence information in the aforementioned processor case may be checked following input, by interaction between the ROM(A) program and the electronic data processor P, to provide a warning signal and/or deactivation (or a zero output) in the event of a problem.

The foregoing safety precaution and checking interactions and capabilities (RAM storage location integrity and checking of sequence information) are conventionally implemented and well-known and understood by those skilled in the art.

Upon completion of the desired interaction, in the so-called "processor" case, between the processor P and the apparatus, the receipt of a termination signal along the serial input line 48 will indicate to the central processing unit CPU that its interaction with the processor P should be ceased. The apparatus may then be electrically decoupled from the processor terminal T. Then, if the patient PT, or the patient together with infusion pump IP, is at a different location, the apparatus may be transported from the location where it was coupled to the processor P to the vicinity of the patient PT, or patient and infusion pump IP, to be coupled to the fluid 14 and to then perform the desired regulating of the flow rate of the fluid 14.

The capability of the apparatus to receive input information from the processor P without a human interface is considered a significant advantage. Thus, where the critical safety concerns of medical apparatus are present, and complicated regimens for using drugs are desired, e.g. including up to 20 flow rates and their durations, it is deemed of great concern from a safety standpoint to not interface an individual in the provision of the sequence information that will control the flow rate of, e.g., a potentially hazardous drug. This is particularly true where the drug may be infused over long periods when an attendant is not present or may be occupied with other duties or when the attendant is not knowledgeable with regard to the treatment or the operation of equipment which is being used. This is particularly critical in the instant situation in which one may desire to provide the patient with the drug treatment without the monitoring that would be required in the absence of apparatus such as the present apparatus having a capability to automatically control a complicated infusion regimen. The capability of the apparatus to be coupled and decoupled to a source processor P, through e.g. a simple connector used in implementing an RS-232C communication protocol (e.g. incorporated in the terminal-CPU interface 24), and to be transported away from the location of such coupling to a location of a patient PT, e.g. in an ambulance, is also considered to be a significant advantage. In implementing this adaptability to transport, or portability, the power supply 26 for the apparatus is of importance.

As in part indicated by FIG. 1, the power supply 26 provides three DC output signals for powering the apparatus. The power signal V1 in FIG. 1, referred to previously, is a "lower" voltage signal, e.g. +5 volts. Two other signals have greater absolute values, e.g. +15 volts. As indicated in FIG. 1, the elements of the apparatus of FIG. 1 are essentially completely powered by only these three power signals. The low power requirement of the apparatus in fact enables the implementation of the power supply 26 with standard alkaline D-cells. Thus, in the apparatus of FIG. 1, the power supply 26 is implemented, with safety requirements in mind, through two separate packs of such D-cells (each pack having a number of cells in series and in parallel to provide adequate voltage and current). Based on the power requirements of the apparatus, eack pack is designed to have a capability to power the apparatus for in the range of 20 hours, providing a total storage capacity sufficient to power the apparatus for at least approximately 30 hours and in fact in the range of 40 hours. (A capacity to so power the apparatus for at least 8 hours would of course cover a typical working shift.) When the first pack becomes low, the power supply will be switched to the second pack along lines which will be explained in more detail below. For the purposes of the present discussion it need only additionally be noted that the ± higher absolute value signals may be readily derived from lower absolute value D-cell voltages through conventional methods, and that two key factors in limiting the power requirements of the apparatus are the liberal use of CMOS technology in implementing the central processing unit CPU and related elements, and the liberal use of liquid crystals in implementing the display panel DP for the apparatus. Such crystals may be used to implement, among other information, alphanumeric information provided by the panel. Certain of the alphanumeric information provided by the display panel DP of FIG. 1 is of some interest and will thus be briefly described. It will be evident that this information is in many respects related to the keyboard initial input and modification processes which have been previously described.

First of all, with respect to the entry of initial sequence information through the keyboard, the display is adapted to provide the following important instructional information: ENTER RATE to indicate to an operator to enter a rate for a sequence position; and ENTER TIME to similarly call for the entry of the duration for a sequence position. Then, generally during regulating operation, which may include the aforementioned modification processes, the display is adapted to provide the following information, some of which relates to keyboard inputs: RUN to indicate the apparatus is operating to regulate the flow rate of a fluid; ENTER GO TO to tell the operator that he has pushed a GO TO keyboard button and should provide the number for the sequence position he wishes to go to in modifying the sequence; ENTER ADJUST to similarly tell the operator he has pushed an ADJUST keyboard button and should now enter the adjustment factor to modify a sequence; ALTERED PROGRAM to indicate that a sequence has been altered by a GO TO or ADJUST; CONTINUE LAST INFUSION to indicate that the sequence calls for continuing the last flow rate in the sequence indefinitely; LAST INFUSION STOP to, by way of contrast, indicate that the sequence information calls for terminating the infusion after a definite infusion interval for the last position in the sequence; END to indicate the end of a sequence has been reached and the infusion has terminated; SERVICE to indicate a divergence in the output from predetermined standards in the RAM 23, tested in a way which will be explained in more detail below; the infusion number in a sequence; the infusion rate entered for that number; any adjustment factor entered in modifying a sequence and the rate entered times the adjustment factor; the total time elapsed since the infusion was commenced; and, available to replace the elapsed time upon triggering of a TOTAL MILLILITERS INFUSED keyboard button, the total volume of fluid infused since the commencement of the sequence.

Of related interest, in addition to the keyboard push buttons and/or push button instructions previously explicitly or implicitly noted, e.g. CLEAR, ENTER, GO TO, ADJUST, TOTAL ML INFUSED, CONTINUE LAST INFUSION, numbers to enter rates and times, POWER to turn on the power to inititate start-up, other buttons (and functions) of note include a START button (and function) to start a regimen, and a STANDBY button (and function) to hold a sequence in suspension to e.g. change a syringe. In addition, an input button (function) capability conveniently called REVIEW is useful to provide a display panel review of the initially input flow rates and durations starting with the first triggering of the button at the first infusion number. Each subsequent triggering would then result in the provision of display information for the next infusion number. A capability may then be included to leave the review procedure without carrying out a full review and to revert to the nonreview display information after an interval (e.g. 20 seconds) following initiation of review. A great many variations in display information and input buttons and functions are of course possible, and may be readily implemented.

Now finally returning to the regulating operation of the apparatus to provide a sequence of flow rates, incorporating the modification features previously noted and initiated through keyboard inputs, such operation can be readily understood by reference to various of the control signals shown in FIG. 1.

Figure 2:
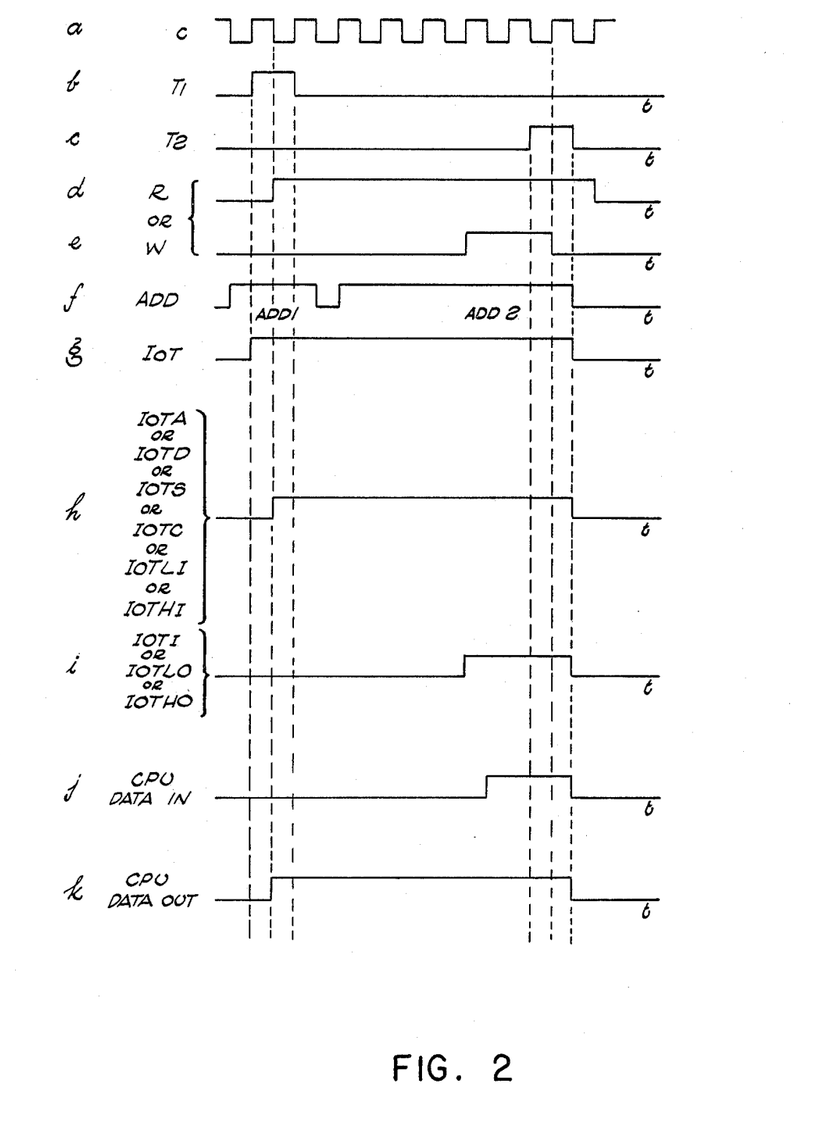
FIG. 2 is an illustrative timing diagram for the apparatus of FIGS. 1A and 1B.

Referring to that figure, the timing for the central processing unit CPU is controlled by a clocking signal C from a conventional crystal clocking unit 30. A clocking signal having a frequency of, for example 2 megahertz, is appropriate for the operation of the system of FIG. 1. A typical clocking signal C, assumed herein to be operative, is represented in FIG. 2(a). The clocking signal controls the output of control signals T1, T2, R and W from the central processing unit CPU.

As shown in FIG. 2(b) and 2(c), the central processing unit places a high pulse along the control signal T1 near the beginning of an 8 clock pulse central processing unit cycle and similarly places a high pulse along the control signal T2 near the end of the cycle. Similarly, as indicated in FIG. 2(d) and 2(e), the central processing unit places a high interval along the control signal R, indicating a "read" interval during a cycle, along an interval starting near the middle of the high pulse along the control signal T1 and ending after the falling edge of the high pulse along the control signal T2, or a high interval along the control signal W, indicating a "write" interval during a cycle, beginning somewhat after the middle of the cycle and ending near the time marking the middle of the high pulse along the control signal T2. Typically, the central processing unit continuously puts out these four control signals, the high pulses along the control signals T1 and T2 occurring for each eight clock pulse cycle, and either the high interval along the control signal R or the high interval along the control signal W occurring during a cycle, but not both.

The interaction between the central processing unit CPU and memory M by which signal-represented information may be transferred between the two elements or by which the memory may be enabled to transmit stored, signal-represented information to various of the other elements or receive signal-represented information from various of the other elements, is readily understood in light of the aforementioned control signals and other timing aspects illustrated in FIG. 2. In FIG. 1, it is assumed that such data communication between the central processing unit and memory, and in fact generally between the memory and other digital elements, is generally in parallel, no more than 8 bits at a time. Other choices are of course readily available and possible.

Proceeding along these lines, the addressing of the desired portion (ROM(A) 42, ROM(B) 44 or RAM 23) and storage location in a portion of the memory M is accomplished, first, by the output by the central processing unit of a number of bits including higher order bits of an address requiring more than 8 bits, which bits are received by an address register in a CPU-memory interface 50 and stored along the rising edge of a high pulse along the control signal T1. These first addressing bits are followed during the same cycle by bits which include the remaining required address information. The timing of the transmittal of both the former and these latter bits is represented in FIG. 2(f), where the interval for transmitting the first part of the addressing information is shown by a portion labeled ADD1 and the interval for the second, by the portion labeled ADD2.

After the CPU-memory interface 50 has stored the first group of bits and received the second group, it may then transmit the full address, requiring both groups, to the memory M. It is noted that the interface need not store the second group of bits. Thus, the full address will be stabilized during a "read" interval somewhat after the commencement of the high period along the control signal R, and during a "write" interval, well before the onset of the high period along the control signal W.

Assuming a "read" interval and the transmittal of information from the memory (e.g. the ROM(A) 42, from a storage location containing an instruction for the central processing unit) to the central processing unit, the central processing unit will be enabled to receive the signal-represented information during a period represented by the high pulse along the timing signal labeled CPU DATA IN in FIG. 2(j), and the memory will be transmitting the correct information after the addressing information has stabilized. An internal data-in register in the CPU may then store this information along the rising edge of a clock pulse occurring while the central processing unit is enabled to receive information (while CPU DATA-IN is high). On the other hand, assuming that information is to be transmitted by the central processing unit to the memory M, the timing signal in FIG. 2(h), labeled CPU DATA OUT, represents, while it is high, an interval during which the central processing unit will be transmitting information; and the desired storage location in the memory may then receive the transmitted information after the onset of the high interval along the control signal W, and store it along the falling edge of the control signal. This sort of interaction is of course well understood. In this regard, it is noted that the functions of a central processing unit such as that in the system of FIG. 1 may be readily implemented using the RCA CDP1802 CMOS Microprocessor. See COSMAC Microprocessor Product Guide (MPG-180A), RCA Corporation, 1977.

In addition to generating the control signals T1, T2, R and W, signal-represented addressing information for the memory, as well as other signals, the central processing unit CPU also transmits control signals IOT to an I/O and testing controller 52. In FIG. 1, these signals are transmitted along a control cable 54, and are assumed to be three signals transmitted in parallel along the control cable. Further, any or all of these signals may have a high interval during any central processing unit cycle, beginning near the rising edge of a high pulse along the control signal T1 and ending near the falling edge of a high pulse along the control signal T2. Also, during any such cycle, all of these signals may lack a high pulse, and thus be in a low state. The timing of a high interval along an IOT control signal is represented in FIG. 2(g). In response to the IOT control signals, the I/O and testing controller 52 may, during a central processing unit cycle, provide a high interval along any one of eight control signals emanating from it which control various of the input and output, as well as safety and testing, functions of the apparatus.

The eight control signals from the I/O and testing controller 52 are logically generated in conventional fashion from the three input IOT control signals from the central processing unit, and from the control signals R, W and T2, also received by the I/O and testing controller 52 from the central processing unit. The three IOT control signals, representing a possible seven alternative combinations in which at least one of the signals has a high interval during a cycle, are each sensed in conventional fashion by the I/O and testing controller 52. The IOT and testing controller in turn provides a high interval along one of six internal signals, each associated with one of six of the combinations which are employed, during essentially the same interval as the one or more IOT control signals are high. These internal signals, which will be generically called IOTG, are used to provide a high interval during a cycle with a "read" interval, along one of the following groups of control signals transmitted by the I/O and testing controller 52: IOTA, IOTD, ITOC, IOTS, IOTLI and IOTHI. In the system of FIG. 1, this is accomplished by the logical operations IOTG and R, performed for each of the internal IOTG signals. Thus, during a "read" cycle, one of the aforementioned group of control signals transmitted by the controller 52 may have the high interval along it represented by the timing diagram of FIG. 2(h). However, of course, one of this group need not necessarily have a high interval during such a "read" cycle. Similarly, three of these same six internal IOG signals are employed to generate high intervals which may occur during "write" cycles along the following control signals transmitted by the I/O and testing controller: IOTI, IOTLO and IOTHO. Such high intervals are accomplished by the logical operations (IOTG AND W) OR T2, performed for each of the group of three signals from the group of IOTG signals. Again, any one of the signals IOTI, IOTLO and IOTHO may have a high pulse during a "write" cycle, as illustrated in FIG. 2(i), but there need not be a high pulse along one of them during such a cycle. The described techniques for providing the control signals tramsitted by the IOT and testing controller 52 are commonly employed; and in light of the above and the later detailed explanation of how such controlled signals are employed, a great many variations which satisfy the requirements herein will be readily apparent.

With the above understanding, the way of accomplishing input, output and various testing and safety functions of present interest is readily understood. The functions referred to encompass the input of information from the input interface 22 to modify (during regulating operation) a flow rate sequence; the receipt and storage of a digitally-represented flow rate from the RAM 23 by a digital to analog conversion system 56 and the conversion of the digitally-represented flow rate signal to an analog signal for output; the selective testing of such signal (and, through this, testing of the signal at the output lines 12), of the generally analog power signal V1, and of the generally analog output signal of the conventionally implemented frequency detector 28, representative of the frequency of the clocking signal C; and the updating of display panel information.

As is evident from the figure and from the above discussion of the control signals provided by the I/O and testing controller 52, the testing may be accomplished by alternative selections by the conventionally implemented analog device selector 31, according to signal-represented device addressing information received from the RAM 23, and by the transmittal of the selected signal to an analog to digital conversion system 60 which, after converting the received analog signal to a digital representation, provides the digital representation to the RAM 23 for comparison by interaction betweeen the central processing unit CPU and memory M, with predetermined standards fo the signal. In the case of the output signal of the digital to analog conversion system 56, the predetermined standard would be the signal-represented information representing the flow rate which had been transmitted to the analog to digital conversion system. In the case of the power supply signal V1, it would be a digitally-represented range of acceptable voltage levels (e.g. 4.75 to 5.00 volts). And in the case of the output signal from the frequency detector 28, it would typically be a digitally-represented range of acceptable frequencies for the clocking signal.

With respect to updating the display, this function is, summarily, accomplished by, first, the receipt and storage of signal-represented addressing information, e.g. for a given digit, by a memory-display and fail safe interface 62, and the subsequent receipt and storage by the interface 62 of signal-represented data, e.g. for this digit, which is then received and stored by the display.

Before addressing these functions and other matters in somewhat more detail, it will be valuable to provide a glossary of various relevant signals, as follows:

| Signal | Source Element | Element(s) To Which Provided | Summary Functional Description |
|---|---|---|---|
| R | CPU | CPU-Memory Interface; Memory; I/O and Testing Controller | Defines "Read" interval during CPU cycle; enables memory to be read |
| W | CPU | CPU-Memory Interface; Memory; I/O and Testing Controller | Defines "Write" interval during CPU cycle; enables memory to store input signal along falling edge of control signal |
| IOTI | I/O and Testing Controller | Input interface | Input register in interface transmits stored input signal while control signal is high. |
| IOTA | I/O and Testing Controller | Memory-Display and Fail Safe Interface | Address register in interface stores display address signal along falling edge of control signal |
| IOTD | I/O and Testing Controller | Memory-Display and Fail Safe Interface | Display register in interface stores display data signal along falling edge of control signal |
| IOTS | I/O and Testing Controller | Analog Device Selector | Address register in selector stores device address signal along falling edge of control signal, selecting analog signal to be transmitted by selector |
| IOTC AND SC | I/O and Testing Controller and Memory (through logic gate) | Analog to Digital conversion system | System starts conversion along falling edge of IOTC AND SC |
| IOTLO | I/O and Testing Controller | Analog to Digital conversion system | System transmits part, including lower order bits, of digital output signal while control signal is high |
| IOTHO | I/O and Testing Controller | Analog to Digital conversion system | System transmits part, including higher order bits, of digital output while control signal is high |
| IOTLI | I/O and Testing Controller | Digital to Analog conversion system | System stores part, including lower order bits, of digital input along falling edge of control signal |
| IOTHI | I/O and Testing Controller | Digital to Analog conversion system | System stores part, including higher order bits, of digital input along falling edge of control signal |
| IOTC AND LCR | I/O and Testing Controller and Memory (through logic gate) | Digital to Analog conversion system | System starts conversion along falling edge of IOTC AND LCR through storage of digital signal for conversion in conversion register in system |
| IOTC AND SBP | I/O and Testing Controller and Memory (through logic gate) | Power Supply | Supply switches to second battery pack along falling edge of IOTC AND SBP |
| FS1 | Memory-Display and Fail Safe Interface (through logic) | Fail Safe Relay Circuitry | Maintains closure of a first relay in circuitry to permit passage of output signal to infusion pump when frequency of high pulses along control signal is sufficient |
| FS2 | Memory-Display and Fail Safe Interface (through logic) | Fail Safe Relay Circuitry | Maintains closure of a second relay in circuitry to permit passage of output signal to infusion pump when frequency of high pulses along control signal is sufficient |
| CI | Interrupt CPU Clocking Unit | | Interrupts CPU along rising edge of control signal to instruct CPU to include input from input interface (if ST signal is high) and display updating in the operations being carried out |

As mentioned earlier, the interaction of the input interface 22 with the memory M, even with an individual rapidly working the keyboard K, would not generally require a capability to receive an input signal by the memory at intervals shorter than 100 milliseconds. Thus, referring to the control signal CI above, an interrupt clocking unit 64 acts along conventional lines in effect as a frequency divider to provide an interrupt clocking signal CI having a frequency, e.g. with a 2 megahertz clocking signal C, of 10 Hertz and a period of 100 milliseconds. Essentially the same situation obtains with the display DP and the memory-display and fail safe interface 62 in that it is not considered necessary to update the display at intervals greater than 100 milliseconds. Thus, the interrupt clocking signal CI to the central processing unit CPU interrupts the central processing unit, e.g. every 100 milliseconds, to initiate a mode of operation of the CPU which will result in the occurrence of high pulses along the control signals IOTI (if ST signal is high), IOTA and IOTD. Only one IOTI high pulse (enabling one occurrence of an input) will occur during the interval; however, a number of IOTA, then IOTD, high pulse sequences will occur during the interval, as the display includes a number of elements (e.g., alphanumeric digits and letters) for which the enabling of updating is required. Thus, the interrupt clocking unit essentially provides a slow clock to control the input of information by and the output of information to an individual. The control signals T1, T2, R and W will of course generally still be operative during the mode of operation triggered by the interrupt clocking signal, and the regulation of the flow rate of the fluid 14 will continue.

The control signals FS1 and FS2 are of great significance from a safety standpoint in that they are signals which check whether the central processing unit is acting in certain undesired ways or modes rather than in expected and desired modes. Thus, as the central processing unit CPU carries out its operations, receiving signal-represented information, transmitting address information and control signals R, W, T1 and T2, and IOT, the central processing unit will if it is not functioning in certain undesired ways, and assuming other "secondary" events related to the FS1 and FS2 signals occur, cause high pulses to occur along the control signals FS1 and FS2 at expected intervals to fail safe relay circuitry 40. This circuitry, implemented along conventional lines (e.g., charge on a capacitor dependent upon frequency of high pulses) will maintain a relay responsive to each of these control signals closed if it receives high pulses along the signal at frequent enough intervals. Each relay, in series with the other relay, will however open if the high pulses are not frequent enough. In this regard, it may be considered desirable to allow for the absence of a number of expected pulses before the relay opens, indicative, e.g., of a clear case of an undesired mode. This checking capability is particularly critical, for in its absence a patient could continue to receive a drug while the system may appear to act generally normally while operating abnormally. Since the control signals FS1 and FS2 relate in some respects to the operation of the memory-display and fail safe interface 62, they will be addressed in more detail after the operation of that interface has been described in connection with the updating of the display.

Somewhat similar concerns are present with regard to the frequency detector 28 and its detection of the frequency of the clocking signal C. As one illustrative example, the clocking unit 30 may fail in a fashion causing its frequency to double. In such a case the system, in the absence of a check stemming from the frequency detector 28, might continue to operate, but at twice the expected rate.

The operation of the digital to analog conversion system 56, analog to digital conversion system 60, analog device selector 31, memory-display and fail safe interface 62 and display panel DP is in large part readily evident by reference to FIG. 1 and the above table. Regarding the digital to analog conversion system 56, during a central processing unit cycle in which the implementation of a flow rate for a new infusion number is to be commenced, the control signal IOTLI will have a high interval which, along its falling edge, will cause a first input register in the system to store input information, including lower order bits of the digital representation to be converted to the analog signal for controlling the flow rate. During a subsequent cycle, which may conveniently be the next cycle, a second input register will store, along the falling edge of the control signal IOTHI, input information, including higher order bits of the just-mentioned digital representation. This two-step transfer is required in FIG. 1 due to the assumption of generally eight-bit parallel communication, and a similar assumption that more than 8 bits are used in the conversion process. Then, during another subsequent cycle, which again may conveniently be the next one, a high interval along the signal IOTC AND LCR from an AND gate 66, along its falling edge, will cause an internal conversion register in the digital to analog conversion system to store both the lower and higher order bits which it receives from the input registers. Bits in this register are the bits upon which the conversion is performed. The high LCR interval is from a high bit in a memory M storage location which is being addressed. The use of memory bits for essentially control purposes, as here, is of some interest; however, satisfactory alternatives, including the incorporation of an additional control signal from the IOT and testing controller 52 are readily apparent.

Now referring to the analog device selector 31, a high interval along the control signal IOTS permits the analog device selector 31 to receive addressing information from the memory representative of an upcoming selection of the power signal V1, of the output signal of the frequency detector 28 or of the output signal of the digital to analog conversion system 56. This addessing information will be stored in an address register in the selector along the falling edge of the control signal IOTS. These events result, along conventionally implemented lines, in the selection by the selector 31 of one of the three generally analog signals for transmittal to the analog to digital conversion system 60. By way of example, it will be assumed that the output of the digital to analog conversion system 56 has just been selected.

During a "read" cycle subsequent to the selection cycle, which could conveniently be the next cycle, a high interval along the control signal IOTC, interacting with a high LCR interval from a bit in an addressed storage location in memory and a second AND gate 68 will, along lines described above with regard to the digital to analog conversion system, commence the analog to digital conversion by the conversion system 60. This will occur along the falling edge of the high IOTC interval. Then, during subsequent "write" cycles, bits, first including lower order bits, and then higher order bits, of the digital representation resulting from the conversion, will be transmitted from an output register in the system for receipt by the RAM 23 and storage by the RAM in addressed storage locations. The first and second of these cycles will, respectively, be characterized by high intervals, enabling the transmittal by the conversion system, along the control signals IOTLO and IOTHO. Following the receipt of the digital representation, the central processing unit CPU and memory M will interact along conventional lines to compare the received information with information already stored in the RAM 23 which was the source of the signal converted to analog form by the digital to analog conversion system 56. In the event of a discrepancy, after the occurrence of the next interrupt of the central processing unit by the interrupt clocking signal, a warning signal, the word SERVICE, will be provided by the display panel, and, in addition, the output of flow rate information to the infusion pump may be ceased—i.e., a zero output level to the infusion pump IP may be established, or deactivation of the output may be implemented, all under the control of the ROM(B) program.

The testing of the output signal from the frequency detector and of the power signal V1 is along analogous lines. However, in these cases, since the standards for the frequency detector output signal and for the power supply signal V1 may be essentially permanently programmed into the system, the predetermined standards may be stored in digitally represented form on a permanent basis in the ROM(B) 44 rather than on a temporary basis in the RAM 23. Also, different warning signals and/or consequences may be provided as noted in connection with the description of the updating of the display, to follow.

Referring to the process of updating the display, as previously noted such updating may occur at intervals, e.g. 100 milliseconds, the onset of such an interval being controlled by the interrupt clocking signal CI. Thus, typically, during a cycle after the onset of an interrupt, the control signal IOTA will go high, causing an address register in the interface to receive signals from the RAM 23 for addressing an element of the display panel DP, and to store such signal along the falling edge of the high interval. Then, during a subsequent, conveniently the next, cycle, a data register in the memory-display interface 62 will similarly receive and store a data signal for that display element. In the case of a liquid crystal display element for a number, to e.g. display the digit 5, a single control bit will be received with the data, causing a high level along the signal CC which will trigger the receipt by the display panel circuitry of the data from the data register, and the subsequent storage (along the falling edge) of the data by a register for that element. The so stored digital signal, in the register for the element, will then determine which liquid crystal portions of the element are excited by the oscillation signals conventionally incorporated into display panel circuitry uitilizing liquid crystals, causing a 5 to appear in that display element. In this regard, it is again noted that successive occurrences of high intervals along the control signals IOTA and IOTD will typically occur after the onset of each interrupt so that many or all of the display elements may be updated essentially every 100 milliseconds.

Besides, e.g. the various alphanumeric information which may be provided by the display panel, the sound alarm 36, first warning light 32 and second warning light 34, previously noted, are also incorporated in the display panel DP of FIG. 1.

In the apparatus of FIG. 1, the first warning light 32 is employed to indicate that the central processing unit has, through the selective testing process described earlier, detected that the first battery pack in the power supply 26 was putting out insufficient power and that as a result, the power supply has received a high IC AND SBP interval during a "read" cycle causing it to switch in the second power supply. The first warning light will then be turned on through addressing and data information channeled through the memory-display and fail safe interface 62, along lines previously noted, with a high CWL interval provided in the same fashion as the aforementioned high CC. Similarly, the second warning light 34 will be similarly activated following the next interrupt after a detection of an input of a rate, through an ADJUST modification, exceeding the maximum of the infusion pump IP, e.g. 99.9 milliliters per hour.

Additionally, the alarm is addressed and activated as a result of an indication, through the selective testing, that the second battery pack is low, or that the frequency of the clocking unit has diverged from the predetermined standards for it. In this regard, the beeping rate of the alarm may be varied to indicate one or the other of these occurrences. Thus, the sound alarm 26 itself has several addresses, the receipt of activating data at one, activating one beeping rate, and the receipt of activating data at the other causing the onset of a second beeping rate. With the occurrence of both conditions, the sum beeping signal will then occur. Alternatively, for example, such rates might be controlled by the rate of channeling of activating data (an activating signal) to a single address for the alarm.

It is also noted that it is considered useful to activate the alarm upon the end of a sequence in which a continuation of the flow rate of the last infusion number has not been indicated. A different beeping frequency then might be employed for this condition. The employment of warning lights, warning sound alarms and alphanumeric warning information (e.g. SERVICE) may of course be varied. For example, the SERVICE alphanumeric information and sound alarm might together be employed to indicate a check sum on the flow rate information in the RAM has come up with a discrepancy with respect to an originally stored sum, or that the output signal of the digital to analog conversion system has become zero or been deactivated as a result of the determination that it did not correspond to the stored, digitally-represented output level in the RAM. Such variations may be readily implemented along the lines described above. Warnings such as the above in effect act as an interface between the selective testing capability and other safety aspects of the apparatus and an individual monitoring the operation of the apparatus, continually or at intervals, and possibly from a distance.

Returning to the control signals FS 1 and FS2, their generation may now readily be understood. Continuing with the assumption of generally 8-bit, parallel communication in the apparatus of FIG. 1, it is further assumed that the number of display elements to be addressed through the address register in the memory-display and fail safe interface 62 does not require more than 6 bits to accomplish the addressing. There will then be at least 2 bits remaining in, e.g., the address code for addressing the last digit in the elapsed time indicated by the display. For example, the address for this digit might be 111010, where the unused bits are of no concern with respect to such addressing.

Utilizing this situation, in FIG. 1, the two otherwise unused bits stored in the memory storage location from which the address for this digit is obtained are assumed to be set to 10, a code essentially arbitrarily chosen. For addressing the other display elements, the unused bits may, for example, be filled with zeros, or codes other than 10. Then, when the element for this digit is addressed, logic circuitry, including a first fail safe AND gate 70 and an inverter 72 will, through the occurrence of a high interval along the control signal FS 1, indicate that the central processing unit CPU has correctly functioned to the extent of reaching this point (as well as that other events required to achieve the high interval have occurred).

Similarly, with respect to the data used in updating, e.g. the last digit in the elapsed time, for which only 4 of 8 available bits will be required, after the storage location for the data to be used for a given update has been determined (by the central processing unit), the central processing unit, under the control of the PROM(B) program, will write an essentially arbitrarily chosen code, assumed to be 1010 in FIG. 1, in the otherwise unused 4 bits. Then a second fail safe AND gate 74 and two associated inverters 76 and 78 will, assuming the required events, including CPU operations, have occurred, cause a high interval along the control signal FS2 as the display data for the digit is provided by the interface to the display. The 4-bit code will be "erased" by the central processing unit from the storage location, under the control of the PROM(B) program, subsequent to its use. It may be appreciated that this check on the desired operation of the central processing unit (as well as other aspects of the apparatus) is perhaps more extensive than that through the control signal FS 1.

Given the foregoing, the control signals FS1 and FS2 may then interact with the fail safe relay circuitry 40 in the manner previously described.

It is noted that, if desired, the control signals FS1 and FS2 could additionally be used to deactivate the output upon the occurrence of other problems in the apparatus (e.g., related to the clocking signal frequency, power signal V1 or output of the analog to digital converter, discovered by selective testing) beyond certain undesired modes of operation of the central processing unit. However, the role of such control signals in checking for such undesired modes of operation which might otherwise go undetected is deemed to be of great importance. From a different perspective, each of the control signals FS1 and FS2 is of course used to indicate the absence of certain undesired modes of operation of the central processing unit CPU.

In view of the above description, it may be seen that the apparatus herein may be variously implemented and variously used depending upon specific applications. For example, the fluid flow rate could alternatively relate to a liquid which is being vaporized for inhalation by a patient; the output to a regulator could indicate a flow rate through its frequency or more directly, through a binary word, which output forms might be accepted by various regulators; control over relatively low rates of flow and small variations might be accomplished by regulation incorporating a piezoelectric material excited in varying degrees; and the regulation could incorporate the use of a bottle for a liquid equipped, for example, with a drip device, a piston-driven cassette drive or a peristaltic pump device. Accordingly, the scope hereof shall not be referenced to the disclosed embodiments, but on the contrary, shall be determined in accordance with the claims as set forth below.

What is claimed is:

1. Portable medical apparatus for controlling the flow rate of a fluid for medically treating a patient according to fluid flow rate information available from an individual, and from a source electronic data processor, the available flow rate information representing sequences of flow rates and their durations, comprising:
   operator input means for coupling to the individual to receive flow rate information provided by the individual and provide electrical signals representative of said information;
   source processor input means for coupling to the source electronic data processor to receive flow rate information provided by the source processor and provide electrical signals representative of said information; and
   electronic data processing means for coupling to said operator input means and to said source processor input means to receive said electrical signals, provide and store storage signals representative of said received electrical signals and provide flow rate output signals, representative of said storage signals, for regulating the flow rate of the fluid;
   said electronic data processing means including means for coupling to infusion regulator means for regulating the flow rate of the fluid in response to said output signals.

2. Controlling apparatus according to claim 1 further comprising:
   infusion regulator means for said coupling to said electronic data processing means to regulate the flow rate of the fluid in response to said output signals.

3. Controlling apparatus according to claim 2 further comprising:
   fluid introduction means for storing the fluid and for coupling to said regulator means and to the patient to provide the fluid to the patient in accordance with said regulating by said regulator means.

4. Controlling apparatus according to claim 1 wherein said source processor input means comprises means for electrically coupling said apparatus to and decoupling said apparatus from the source electronic data processor.

5. Controlling apparatus according to claim 1 wherein said electronic data processing means further comprises a portable power supply having a power capacity sufficient to power said apparatus.

6. Controlling apparatus according to claim 1 wherein said electronic data processing means further comprises:
   means for providing control signals for controlling operations of said apparatus, said control signals including at least one signal for indicating an undesired mode of operation of said means for providing; and
   means for interrupting the provision of said output signals of said data processing means in response to an indication of a said undesired mode of operation by said control signal.

7. Controlling apparatus according to claim 1 wherein said electronic data processing means further comprises:
   means for providing a clocking signal for said data processing means; and
   a frequency detector, electrically coupled to said clocking signal providing means, for providing a detector output signal representative of the frequency of said clocking signal in response to said clocking signal.

8. Controlling apparatus according to claim 1 wherein said electronic data processing means further comprises:
a portable power supply for providing at least one electrical output signal for powering said apparatus; and
means for selectively testing said output signals of said electronic data processing means and power supply against predetermined standards and for providing a warning signal to an operator of said apparatus in the event of divergence from said standards.

9. Controlling apparatus according to claim 1 wherein said electronic data processing means further comprises:
a portable power supply for providing at least one electrical output signal for powering said apparatus;
means for providing a clocking signal for said electronic data processing means;
a frequency detector, electrically coupled to said clocking signal providing means, for providing a detector output signal representative of the frequency of said clocking signal in response to said clocking signal; and
means for selectively testing said output signals of said electronic data processing means, power supply and frequency detector against predetermined standards and for providing a warning signal to an operator of said apparatus in the event of divergence from said standards.

10. Portable medical apparatus for controlling the flow rate of a fluid for medically treating a patient according to fluid flow rate information available from an individual, and from a source electronic data processor, the available flow rate information representing sequences of flow rates and their durations, comprising:
operator input means for coupling to the individual to receive flow rate information provided by the individual and provide electrical signals representative of said information;
source processor input means for coupling to the source electronic data processor to receive flow rate information provided by the source processor and provide electrical signals representative of said information, and
electronic data processing means for coupling to said operator input means and to said source processor input means to receive said electrical signals, provide storage signals representative of said received electrical signals, store simultaneously storage signals representative of a sequence of fluid flow rates and their durations and provide flow rate output signals, representative of said storage signals, for regulating the flow rate of the fluid;
said electronic data processing means including means for coupling to infusion regulator means for regulating the flow rate of the fluid in response to said output signals.

11. Controlling apparatus according to claim 10 wherein said apparatus is decouplable from the source electronic data processor to regulate the flow rate of the fluid independently of the source electronic data processor in accordance with a sequence of flow rates and their durations determined by flow rate information received by said source processor input means from the source electronic data processor.

12. Controlling apparatus according to claim 11 wherein said electronic data processing means comprises a portable power supply having a power capacity sufficient to power said apparatus.

13. Controlling apparatus according to claim 11 wherein said electronic data processing means further comprises memory means for simultaneously storing storage signals representative of a sequence of at least eight flow rates and their durations.

14. Controlling apparatus according to claim 13 wherein said electronic data processing means further comprises a portable power supply having a power storage capacity sufficient to power said apparatus for a sequence duration of at least eight hours.

15. Controlling apparatus according to claim 10 wherein said electronic data processing means comprises a portable power supply having a power capacity sufficient to power said apparatus.

16. Medical apparatus for use with a programmable infusion device for controlling the flow rate of a fluid for medically treating a patient, comprising:
storage means for storing electrical signals representative of successive stages of a sequence of discrete flow rates for said fluid and their durations and for storing electrical parameter comparison signals;
execution means, electrically coupled to said storage means, for automatically providing an output signal corresponding to said stages of said sequence to the infusion device in response to said stored signals upon initiation of said providing by said execution means, said execution means including means for coupling said execution means to the infusion device;
a power supply for providing at least one electrical output signal for powering said apparatus; and
means for selective coupling to said execution means and to said power supply to selectively test said output signal of said execution means and of said power supply against a respective said comparison signal to detect divergences of said output signals from determined standards during said successive stages of said sequence.

17. Controlling apparatus according to claim 16 wherein said power supply is a portable power supply having a power capacity sufficient to power said apparatus.

18. Medical apparatus for use with a programmable infusion device for controlling the flow rate of a fluid for medically treating a patient, comprising:
storage means for storing electrical signals representative of successive stages of a sequence of discrete flow rates for said fluid and their durations and for storing electrical parameter comparison signals;
execution means, electrically coupled to said storage means, for automatically providing an output signal corresponding to said stages of said sequence to the infusion device in response to said stored signals upon initiation of said providing by said execution means, said execution means including means for coupling said execution means to the infusion device;
means for providing a clocking signal for said execution means;
a frequency detector, electrically coupled to said clocking signal providing means, for providing a detector output signal representative of the frequency of said clocking signal in response to said clocking signal; and means for selective coupling to said execution means and to said frequency detector to selectively test said output signal of said execution means and of said frequency detector against a respective said comparison signal to detect divergences of said output signals from determined standards during said successive stages of said sequence.

19. Medical apparatus for use with a programmable infusion device for controlling the flow rate of a fluid for medically treating a patient, comprising:

storage means for storing electrical signals representative of successive stages of a sequence of discrete flow rates for said fluid and their durations and for storing electrical parameter comparison signals;

execution means, electrically coupled to said storage means, for automatically providing an output signal corresponding to said stages of said sequence to the infusion device in response to said stored signals upon initiation of said providing by said execution means, said execution means including means for coupling said execution means to the infusion device;

a power supply for providing at least one electrical output signal for powering said apparatus;

means for providing a clocking signal for said execution means;

a frequency detector, electrically coupled to said clocking signal providing means, for providing a detector output signal representative of the frequency of said clocking signal in response to said clocking signal; and means for selective coupling to said power supply and to said frequency detector to selectively test said output signal of said power supply and of said frequency detector against a respective said comparison signal to detect divergences of said output signals from determined standards during said successive stages of said sequence.

20. Medical apparatus for use with a programmable infusion device for controlling the flow rate of a fluid for medically treating a patient, comprising:

storage means for storing electrical signals representative of successive stages of a sequence of discrete flow rates for said fluid and their durations and for storing electrical parameter comparison signals;

execution means, electrically coupled to said storage means, for automatically providing an output signal corresponding to said stages of said sequence to the infusion device in response to said stored signals upon initiation of said providing by said execution means, said execution means including means for coupling said execution means to the infusion device;

a power supply for providing at least one electrical output signal for powering said apparatus;

means for providing a clocking signal for said execution means;

a frequency detector, electrically coupled to said clocking signal providing means, for providing a detector output signal representative of the frequency of said clocking signal in response to said clocking signal; and means for selective coupling to said execution means, to said power supply and to said frequency detector to test said output signal of said execution means, of said power supply and of said frequency detector against a respective said comparison signal to detect divergences of said output signals from determined standards during said successive stages of said sequence.

21. Medical apparatus for use with a programmable infusion device for controlling the flow rate of a fluid for medically treating a patient, comprising:

storage means for storing electrical signals representative of successive stages of a sequence of discrete flow rates for said fluid and their durations;

execution means, electrically coupled to said storage means, for providing at least one operational output signal for operating said execution means, and for automatically providing an execution means output signal corresponding to said stages of said sequence to control the infusing of the infusion device in accordance with said sequence in response to said stored signals upon initiation of said providing of said execution means output signal by said execution means, said execution means including means for coupling said execution means to the infusion device; and means for selectively testing a plurality of said output signals against standards for said signals set in said apparatus to detect divergences of said output signals from said standards during said successive stages of said sequence.

22. Controlling apparatus according to claim 21 wherein said storage means has a storage capacity for storing electrical signals representative of at least eight successive stages of said sequence.

23. Portable medical apparatus for controlling the flow rate of a fluid for medically treating a patient according to fluid flow rate information available from a source electronic data processor, the available flow rate information representing sequences of flow rates and their durations, comprising:

source processor input means for coupling to the source electronic data processor to receive flow rate information provided by the source processor and provide electrical signals representative of said information; and electronic data processing means for coupling to said source processor input means to receive said electrical signals, provide and store storage signals representative of said received electrical signals and provide flow rate output signals, representative of said storage signals, for regulating the flow rate of the fluid, said electronic data processing means including control means for said processing means and memory means for programming said processing means;

said electronic data processing means further including means for coupling to infusion regulator means for regulating the flow rate of the fluid in response to said output signals.

24. Controlling apparatus according to claim 23 further comprising:

infusion regulator means for said coupling to said electronic data processing means to regulate the flow rate of the fluid in response to said output signals.

* * * * *

UNITED STATES PATENT AND TRADEMARK OFFICE
CERTIFICATE OF CORRECTION

PATENT NO. : 4,308,866
DATED : January 5, 1982
INVENTOR(S) : Roger W. Jelliffe and Jack D. Crone It is certified that error appears in the above-identified patent and that said Letters Patent are hereby corrected as shown below:

Column 1, Line 15, delete "annd" and insert therefor --and--.

Column 1, Line 68, delete "'-".

Column 2, Line 1, delete "'Automated" and substitute therefor --"Automated--.

Column 3, Line 23, delete "times" and substitute --items--.

Column 8, Line 63, delete "+15" and substitute --$\pm$15--.

Column 9, Line 5, delete "eack" and substitute --each--.

Column 13, Line 23, delete "betweeen" and substitute --between--.

Column 13, Line 24, delete "fo" and substitute --for--.

Column 17, Line 33, add --of-- after "intervals".

Column 18, Line 64, before "111010" add -- __ --.

Column 21, Line 49, after "information", delete "," and substitute --;--.

Signed and Sealed this

Twenty-ninth Day of June 1982

[SEAL]

Attest:

GERALD J. MOSSINGHOFF

Attesting Officer      Commissioner of Patents and Trademarks